United States Patent [19]

Oh et al.

[11] Patent Number: 5,268,293
[45] Date of Patent: Dec. 7, 1993

[54] **STRAIN OF *CORYNEBACTERIUM GLUTAMICUM* AND METHOD FOR PRODUCING L-LYSINE**

[75] Inventors: Jong W. Oh, Seoul; Seong J. Kim; Young J. Cho, both of Kyunggi-do; Nai H. Park; Jae H. Lee, both of Seoul, all of Rep. of Korea

[73] Assignee: Cheil Sugar Co., Ltd., Seoul, Rep. of Korea

[21] Appl. No.: 851,120

[22] Filed: Mar. 16, 1992

Related U.S. Application Data

[63] Continuation of Ser. No. 500,304, Mar. 28, 1990, abandoned.

[30] Foreign Application Priority Data

Mar. 30, 1989 [KR] Rep. of Korea ............... 89-4136

[51] Int. Cl.$^5$ .................... C12N 1/20; C12P 13/08
[52] U.S. Cl. ................... 435/252.1; 435/115; 435/843
[58] Field of Search ............ 435/252.1, 843, 115

[56] References Cited

U.S. PATENT DOCUMENTS

| | | | |
|---|---|---|---|
| 3,707,441 | 12/1972 | Shiio et al. | 435/115 |
| 3,708,395 | 1/1973 | Nakayama et al. | 435/115 |
| 3,959,075 | 5/1976 | Inuzuka et al. | 435/115 |

FOREIGN PATENT DOCUMENTS

| | | |
|---|---|---|
| 57-14839 | 1/1982 | Japan . |
| 57-9797 | 2/1982 | Japan . |
| 61-35840 | 2/1986 | Japan . |

*Primary Examiner*—Douglas W. Robinson
*Assistant Examiner*—Marian C. Knode
*Attorney, Agent, or Firm*—Finnegan, Henderson, Farabow, Garrett & Dunner

[57] ABSTRACT

Disclosed are *Corynebacterium glutamicum* CS-755 (KFCC 10672, FERM BP-2763), a L-lysine producing microorganism which is resistant to α-amino-β-hydroxyvaleric acid, S-(β-aminoethyl)-L-cysteine, methyl lysine, arginine analogues, other analogues, β-(2-thiazolyl)-DL-alanine, 5-hydroxyuridine, 6-azauracil, and 6-fluorotryptophan requires leucine and homoserine for growth, and a method for producing L-lysine comprising culturing the strain (KFCC 10672, FERM BP-2763) and recovering L-lysine from the resultant culture broth.

2 Claims, No Drawings

STRAIN OF *CORYNEBACTERIUM GLUTAMICUM* AND METHOD FOR PRODUCING L-LYSINE

This application is a continuation, of application Ser. No. 07/500,304 filed Mar. 28, 1990, now abandoned.

BACKGROUND OF THE INVENTION

The present invention relates to a microorganism capable of producing L-lysine and a method for producing L-lysine thereby. More specifically, the present invention relates to a strain possessing resistance to arginine analogues and other analogues besides the characteristics known as necessary for the production of L-lysine, and a method for producing L-lysine comprising culturing the strain in a nutrient culture medium and recovering L-lysine from the culture broth.

L-Lysine, which is one of essential amino acids, has been used as an animal feed supplement because of its ability to improve the quality of feed by increasing the absorption of other amino acids, and used as a food supplement as well. L-Lysine has been used also in medicine, particularly as ingredients of infusion solutions.

L-Lysine can be produced by fermentation using an auxotrophic mutant and/or regulatory mutant, or by enzymatic conversion which comprises treating DL-$\alpha$-amino-$\beta$-caprolactam (hereinafter referred to as ACL) with L-ACL-hydrolase and ACL-racemase. For commercial production of L-lysine, however, fermentation processes have been more predominantly employed. For example, Japanese Patent Laid-Open No. 82-9797, and Japanese Patent Publication Nos. 82-14839 and 86-35840 disclose the methods using strains having characteristics of vitamin $B_1$, pantothenic acid and/or biotin requirement for growth; resistance to lysine, threonine and/or isoleucine analogues; resistance to one or more antibiotics e.g. bacitracin, penicillin G and/or polymyxin.

SUMMARY OF THE INVENTION

One object of the present invention is to provide a microorganism possessing the resistance to $\alpha$-amino-$\beta$-hydroxyvaleric acid, S-($\beta$-aminoethyl)-L-cysteine, methyl lysine, arginine analogues and other analogues, such as $\beta$-(2-thiazolyl)-DL-alanine, canavanine, cadaverine, spermine, spermidine, putrescine, 5-hydroxyuridine arginine hydroxamate, 6-azauracil, 6-fluorotryptophan, and the leucine and homoserine requirement.

The other object of the present invention is to provide a method which comprises culturing the microorganism described above and recovering L-lysine from the resultant culture broth.

DESCRIPTION OF THE PREFERRED EMBODIMENTS

The present inventors studied *Corynebacterium glutamicum* YJ-150 (deposited in Korean Federation of Culture Collection, on Jun. 21, 1979, with an accession number KFCC 10014), which possessed the characteristics known to be necessary for the production of L-lysine. It was found that when resistance to at least one arginine analogue is conferred on the strain KFCC 10014, L-lysine productivity of the strain increased significantly.

In the present invention any microorganism can be used if the strain belongs to the species *Corynebacterium glutamicum* and possesses the characteristics known as necessary for the production of L-lysine. Therefore, not only strains having such characteristics reported already as the nutrient requirement (homoserine, alanine, leucine, valine, nicotinic acid, pantothenic acid and mixture thereof) and the resistance to various amino acid derivatives (lysine, threonine, methionine, isoleucine, valine derivatives and mixtures thereof), but also strains having the resistance to other amino acid analogues or the resistance to chemicals including antibiotics can be used for L-lysine production. The arginine analogues and other analogues include $\beta$-2-thiazolyl-DL-alanine, canavanine, cadaverine, spermine, spermidine, putrescine, 5-hydroxyuridine, arginine hydroxamate, 6-azauracil and 6-fluorotryptophan.

*Corynebacterium glutamicum* YJ-150 (KFCC 10014) is mutated by suspending the strain (KFCC 10014) in 0.1M magnesium sulfate solution ($10^7 \sim 10^8$ cells/ml) and exposing to ultraviolet(UV) radiation for 30 ~ 180 sec. Otherwise, *Corynebacterium glutamicum* YJ-150 (KFCC 10014) may be mutated by suspending the strain (KFCC 10014) in phosphate buffer(pH 7.0) or citrate buffer (pH 5.5) ($10^7 \sim 10^8$ cells/ml) and treating with 200 ~ 500 $\mu$g/ml N-methyl-N'-nitro-N-nitrosoguanidine(NTG) at room temperature or 32° C. for 10 ~ 30 min. The resultant suspension is then plated onto a minimal agar plate containing 1 ~ 10 g/l arginine analogues and other analogues, and incubated at 32° C. for 4 ~ 7 days to obtain the mutants.

If necessary, after mutation, the mutants are enriched by cultivating in minimal medium containing appropriate amino acids in a hypertonic medium containing 2,000 ~ 10,000 units/ml penicillin G, 0.1M magnesium sulfate and 20% sucrose, and the culture is then plated onto a suitable agar plate to obtain colonies.

The minimal medium is composed of the following:

| Glucose | 10 g/l |
| --- | --- |
| Ammonium sulfate | 2 g/l |
| Urea | 2 g/l |
| $KH_2PO_4$ | 0.2 g/l |
| $K_2HPO_4$ | 0.2 g/l |
| $MgSO_4$ $7H_2O$ | 0.1 g/l |
| $CaCl_2$ $2H_2O$ | 0.1 g/l |
| Biotin | 100 $\mu$g/l |
| Thiamine · HCl | 100 $\mu$g/l |
| $Na_2B_4O_7$ $10H_2O$ | 80 $\mu$g/l |
| $(NH_4)_6Mo_7O_{27}$ $4H_2O$ | 40 $\mu$g/l |
| $ZnSO_4$ $7H_2O$ | 10 $\mu$g/l |
| $CuSO_4$ $5H_2O$ | 300 $\mu$g/l |
| $MnCl_2$ $4H_2O$ | 10 $\mu$g/l |
| $FeCl_3$ $6H_2O$ | 1 mg/l |

Amino acids in the range 50 ~ 100 mg/l were supplemented to the above minimal medium.

Auxotrophic properties and analogue resistances of the strain obtained are confirmed by a replica method, or by evaluating relative growth rates or enzyme activities in flask cultures.

The strain which processed the homoserine and leucine requirement and the resistance to S-($\beta$-aminoethyl)-L-cysteine, $\alpha$-amino-$\beta$-hydroxyvaleric acid, methyl lysine and arginine analogues and other analogues such as $\beta$-(2-thiazolyl)-DL-alanine, canavanine, cadaverine, spermine, spermidine, putrescine, 5-hydroxyuridine and arginine hydroxamate, 6-azauracil and 6-fluorotryptophan, was selected and named *Corynebacterium glutamicum* CS-755. We deposited *Corynebacterium glutamicum* CS-755 in Korean Federation of Culture Collection with the accession number of KFCC-10672 on Mar. 29, 1989 and in Fermentation Research Institute, Agency of Industrial Science and Technology with the accession number of FERM BP-2763 on Feb. 20, 1990.

For L-lysine fermentation, the strain (KFCC 10672, FERM BP-2763) is cultured under aerobic conditions (250~300 rpm in a rotary shaker or 0.5~1.5 vvm of aeration rate in a fermentation jar) at 25°~35° C. adjusting the pH of the culture medium in the range 5.0~8.0. After 48~72 hours, L-lysine is accumulated significantly in the culture broth. When a jar fermentor is used for the L-lysine production, fermentation can be carried out in a fed-batch mode by supplementing additional sugar to the culture broth during cultivation. In the present invention, fermentation performances are evaluated from fed-batch fermentations.

The fermentation medium is composed of the following;

| | |
|---|---|
| Glucose | 75 g/l |
| Ammonium sulfate | 40 g/l |
| CaCO$_3$ | 40 g/l |
| Corn Steep Liquor | 100 g/l |
| KH$_2$PO$_4$ | 1 g/l |
| MgSO$_4$ 7H$_2$O | 0.4 g/l |
| FeSO$_4$ 7H$_2$O | 0.01 g/l |
| MnSO$_4$ 4H$_2$O | 6 mg/l |
| Biotin | 300 μg/l |
| Thiamine · HCl | 500 μg/l |
| Pantothenic acid | 0.01 g/l |
| pH 7.6~8.0 | |

The concentration of L-lysine (as mono-hydrochloride salt) accumulated in the culture broth is analyzed by the acidic ninhydrin method or HPLC, and amino acid composition in the culture broth is analyzed with an amino acid autoanalyzer.

EXAMPLE 1

*Corynebacterium glutamicum* YJ-150(KFCC 10014) was cultivated in a 30-L Jar fermentor at 32° C., pH 6.8~7.0 under 0.5~1.0 vvm of aeration rate. The amino acid composition of culture broth was analyzed with an amino acid autoanalyzer as shown in Table I. To investigate the effects of various amino acids on the L-lysine production, the strain YJ-150 (KFCC 10014) was cultured for 48 hours in a medium containing specific amino acid in 1 g/l and 3 g/l. The results are shown in Table II.

TABLE I

| + Amino acid composition in the culture broth of *Corynebacterium glutamicum* YJ-150 | | | |
|---|---|---|---|
| Amino Acid | g/l | Amino Acid | g/l |
| L-Lysine · HCl | 90.5 | Glutamic acid | trace |
| Alanine | 1.2 | Leucine | 1.8 |
| Valine | 0.5 | Arginine | trace |
| Glycine | 0.5 | Isoleucine | trace |
| Phenylalanine | trace | | |

TABLE II

Effect of various amino acids on L-lysine · HCl production with strain YJ-150

| | L-lysine · HCl produced (g/l) | |
|---|---|---|
| Amino Acid added | 1 g/l | 3 g/l |
| L-Alanine | 16.0 | 17.2 |
| L-Arginine | 19.5 | 20.2 |

TABLE II-continued

Effect of various amino acids on L-lysine · HCl production with strain YJ-150

| | L-lysine · HCl produced (g/l) | |
|---|---|---|
| Amino Acid added | 1 g/l | 3 g/l |
| L-Aspartic acid | 17.2 | 17.5 |
| L-Cysteine | 16.9 | 17.4 |
| L-Glutamic acid | 17.2 | 17.7 |
| L-Glutamine | 17.5 | 17.4 |
| L-Glycine | 17.5 | 18.1 |
| L-Histidine | 18.1 | 18.4 |
| L-Homoserine | 17.4 | 17.3 |
| L-Isoleucine | 18.1 | 17.6 |
| L-Leucine | 15.1 | 14.7 |
| L-Lysine | 17.2* | 17.4* |
| L-Methionine | 17.5 | 17.3 |
| L-Phenylalanine | 17.0 | 17.2 |
| L-Proline | 16.9 | 17.2 |
| L-Serine | 17.4 | 17.3 |
| L-Threonine | 17.5 | 17.9 |
| L-Tryptophan | 16.9 | 17.1 |
| L-Tyrosine | 17.0 | 17.2 |
| L-Valine | 17.9 | 18.2 |

Note>*: Net L-lysine · HCl produced.

From the results shown in Table II, it was found that the production of L-lysine was increased when one of certain amino acids such as arginine, aspartic acid, isoleucine or valine was added, while the production of L-lysine was decreased when leucine was added.

Growth inhibition of *Corynebacterium glutamicum* YJ-150 at various concentrations of S-(β-aminoethyl)-L-cysteine (AEC), an L-lysine analogue, and the effect of arginine addition on the growth were investigated, as illustrated in Table III.

TABLE III

| The resistance to AEC for *Corynebacterium glutamicum* YJ-150 (unit: relative growth ratio, %) | | | | | | |
|---|---|---|---|---|---|---|
| Addition of Amino Acid | AEC added (g/l) | | | | | |
| | 0 | 2.5 | 5 | 10 | 15 | 20 |
| No addition | 100 | 99 | 85 | 65 | 63 | 62 |
| Arginine (1 g/l) | 100 | 99 | 93 | 78 | 78 | 75 |

As shown in Table III, the degree of growth inhibition caused by AEC was reduced when 1 g/l of arginine was added to the culture medium.

From the above results, it was found that the production of L-lysine would increase if a strain possessing resistance to arginine analogues was used. The arginine analogue-resistant mutants were obtained according to the procedure shown in Example 2 and L-lysine productivities of the strains were determined.

EXAMPLE 2

*Corynebacterium glutamicum* YJ-150 (KFCC 10014) was mutated by suspending the strain (KFCC 10014) in 0.1M magnesium sulfate solution at a density of $10^7 \sim 10^8$ cells/ml and exposing to UV-ray for 30~180 sec, or by suspending the strain (KFCC 10014) in phosphate buffer (pH 7.0) or citrate buffer (pH 5.5) at a density of $10^7 \sim 10^8$ cells/ml and treating with 200~500 μg/ml of N-methyl-N'-nitro-N-nitrosoguanidine at room temperature or 32° C. for 10~30 min.

As a result, the L-lysine producing strains having various metabolism-controlled characteristics were obtained as summarized in Table IV.

TABLE IV

L-Lysine producing strains and their characteristics

| Strain | Parent Strains | Characteristics |
|---|---|---|
| Corynebacterium glutamicum CS-1 | YJ-150 | Hse$^-$, AEC$^r$, Arg analogues$^r$ and other analogues$^r$ |
| Corynebacterium glutamicum CS-2 | YJ-150 | Hse$^-$, AEC$^r$, Leu$^-$ |
| Corynebacterium glutamicum CS-3 | CS-1 | Hse$^-$, AEC$^r$, Arg analogues$^r$ and other analogues$^r$, AHV$^r$ |
| Corynebacterium glutamicum CS-4 | CS-1 | Hse$^-$, AEC$^r$, Arg analogues$^r$ and other analogues$^r$, ML$^r$ |
| Corynebacterium glutamicum CS-5 | CS-3, CS-4 | Hse$^-$, AEC$^r$, Arg analogues$^r$ and other analogues$^r$, AHV$^r$, ML$^r$ |
| Corynebacterium glutamicum CS-6 | CS-2 | Hse$^-$, Leu$^-$, AEC$^r$, Arg analogues$^r$ and other analogues$^r$ |
| Corynebacterium glutamicum CS-7 | CS-6 | Hse$^-$, Leu$^-$, AEC$^r$, AHV$^r$, ML$^r$, Arg analogues$^r$ and other analogues$^r$ |

Note>
Hse: Homoserine
Leu: leucine
ML: methyl lysine
AEC: S-($\beta$-aminoethyl)-L-cysteine
AHV: $\alpha$-amino-$\beta$-hydroxyvaleric acid
Arg analogues and other analogues; $\beta$-(2-thiazolyl)-DL-alanine, canavanine, cadaverine, spermine, spermidine, putrescine, 5-hydroxyuridine, arginine hydroxamate, 6-azauracil and 6-fluorotryptophan To evaluate the mutant strains obtained, 20 ml of nutrient medium containing 200 mg/l of the required amino acids was prepared in a 250 ml flask. One loopful of each strain in Table IV grown in a nutrient agar plate was inoculated into the medium and cultivated for 48~72 hours. The L-lysine accumulated was analyzed to select Corynebacterium glutamicum CS-755 (KFCC 10672, FERM-BP-2763) possessing the characteristics such as Hse$^-$, Leu$^-$, AEC$^r$, AHV$^r$, ML$^r$, $\beta$-(2-thiazolyl)-DL-alanine$^r$, canavanine$^r$, cadaverine$^r$, spermine$^r$, spermidine$^r$, putrescine$^r$, 5-hydroxyuridin$^r$, arginine hydroxamate$^r$, 6-azauracil$^r$ and 6-fluorotryptophan$^r$ from Corynebacterium glutamicum CS-7 colonies.

Corynebacterium glutamicum YJ-150 and CS-755 were cultured in flasks, and the amounts of L-lysine produced and the yields calculated were shown in Table V.

TABLE V

Results of the fermentations with Corynebacterium glutamicum YJ-150 and CS-755 in flasks

| Strain used | L-lysine · HCl produced (g/l) | Yield of L-lysine based on the consumed sugar (%) | Growth (OD$_{562}$ × 100) |
|---|---|---|---|
| YJ-150 | 30 | 40 | 0.39 |
| CS-755 | 34 | 45 | 0.32 |

EXAMPLE 3

Fed-batch fermentations were carried out in a 30-L jar fermentor with Corynebacterium glutamicum CS-755 and YJ-150 (parent strain of CS-755). The amount of L-lysine produced and the amino acid composition in the resultant culture broth are shown in Table VI and Table VII, respectively.

TABLE VI

Results of the fermentation with Corynebacterium glutamicum CS-755 and YJ-150 in 30-L jar fermentor

| Strain used | L-lysine · HCl produced (g/l) | Growth (OD$_{562}$ × 100) |
|---|---|---|
| YJ-150 | 92 | 0.90 |
| CS-755 | 120 | 0.81 |

TABLE VII

Amino acid composition in the culture broth of Corynebacterium glutamicum CS-755

| Amino Acid | Amount produced (g/l) | Amino Acid | Amount produced (g/l) |
|---|---|---|---|
| L-Lysine · HCl | 120 | Glutamic acid | trace |
| Alanine | 0.8 | Leucine | trace |
| Valine | 0.3 | Arginine | 2.5 |
| Glycine | 0.1 | Isoleucine | trace |
| Phenylalanine | trace | | |

As shown in Table VI and VII, Corynebacterium glutamicum CS-755 produced up to 120 g/l of L-lysine.HCl. The product yield of L-lysine.HCl based on the sugar consumed was about 45%, and 1.6~2.5 g/l arginine was accumulated in the culture broth.

EXAMPLE 4

10 l of the culture broth obtained by culturing Corynebacterium glutamicum CS-755 (KFCC 10672, FERM BP-2763) was subjected to adjusting the pH with sulfuric acid, and adsorbed on a strong acidic cation exchange resin Duolite C-20N by loading from bottom to top of a column at a space velocity of 5. When this upflow adsorption method was employed, the apparatus such as centrifuges for removing microorganisms from culture broth was unnecessary, and therefore, loss of L-lysine resulting from the operation could be reduced thereby.

After completing the adsorption, the resin column was sufficiently washed with water to remove microorganisms and particulate materials. The L-lysine adsorbed was eluted with 2N-NH$_4$OH and the L-lysine fraction which is 0.6 fold of the resin volume was collected (L-lysine.HCl concentration was 129 g/l, recovery yield from culture broth was 97%). The fractions with low L-lysine concentration were recycled back to the next cycle.

The L-lysine rich fraction was concentrated and removed ammonia, subjected to adjusting the pH at 5.0 by using hydrochloric acid and treated with active carbon. The resultant solution was concentrated further and then filtered to collect the resulting crude crystals (primary crystals). The primary liquid fraction obtained from the filtration was concentrated and then separated again into crystals (secondary crystals) and secondary liquid fractions. The secondary crystals were mixed with the L-lysine rich fraction of next cycle eluted from the resin column described above. The secondary liquid fraction was recycled back to a culture broth tank.

The crystals obtained by the above method were dried in hot air to prepare 993 g of L-lysine hydrochloride (recovery yield was 94%, purity was above 99.5%).

EXAMPLE 5

For 10 l of the culture broth obtained by culturing Corynebacterium glutamicum CS-755 (KFCC 10672, FERM BP-2763) bacterial cells were removed by ultrafiltration (X-Flo system Biorecovery Co. in U.S.A., MRC-Membrane M.W. Cut off 30,000). Total volume of the ultrafiltered culture broth was 35 l. The filtrate was adjusted at pH 5.0, decolorized by active carbon, concentrated, crystallized and then separated into crystals and liquid fraction. The liquid fraction was treated according to the procedure shown in Example 4 to obtain the L-lysine rich fraction. After removing ammonia, the L-lysine rich fraction was mixed with the filtrate in the ultrafiltration step and subjected to pH adjusting, decolorizing and concentrating to obtain 993 g of the pure crystal (recovery yield was 94%, purity was above 99%).

We claim:

1. A *Corynebacterium glutamicum* strain CS-755 (KFCC 10672, FERM BP-2763).

2. A method for producing L-lysine by a fermentation process comprising culturing the *Corynebacterium glutamicum* strain CS-755 (KFCC 10672, FERM BP-2763) in a medium containing assimilable amounts of nutrients for the production of L-lysine, and recovering L-lysine from the culture medium.